(12) United States Patent
Straehle et al.

(10) Patent No.: US 7,369,306 B2
(45) Date of Patent: May 6, 2008

(54) IMAGE REVERSION SYSTEM, ANCILLARY OPHTHALMOSCOPY MODULE AND SURGICAL MICROSCOPE

(75) Inventors: Fritz Straehle, Heubach (DE); Peter Reimer, Ellwangen (DE); Klaus Gottwaldt, Oberkochen (DE); Franz Merz, Aalen (DE)

(73) Assignee: Carl-Zeiss-Stiftung, Heidenheim-Brenz (DE)

( * ) Notice: Subject to any disclaimer, the term of this patent is extended or adjusted under 35 U.S.C. 154(b) by 0 days.

(21) Appl. No.: 10/396,383

(22) Filed: Mar. 26, 2003

(65) Prior Publication Data

US 2003/0165012 A1   Sep. 4, 2003

Related U.S. Application Data

(63) Continuation of application No. PCT/EP01/10094, filed on Sep. 1, 2001.

(30) Foreign Application Priority Data

Sep. 26, 2000  (DE) .................. 100 47 617
Aug. 17, 2001  (DE) .................. 101 40 402

(51) Int. Cl.
    *G02B 21/18* (2006.01)
(52) U.S. Cl. .............. 359/381; 359/372; 359/374; 359/432
(58) Field of Classification Search ........ 359/831–837, 359/420–422, 431–433, 372, 374, 381
    See application file for complete search history.

(56) References Cited

U.S. PATENT DOCUMENTS

| | | | | |
|---|---|---|---|---|
| 2,937,570 A | * | 5/1960 | Hillman | 359/426 |
| 4,702,570 A | * | 10/1987 | Yoshino et al. | 359/377 |
| 4,723,842 A | * | 2/1988 | Twisselmann et al. | 359/372 |
| 5,009,487 A | | 4/1991 | Reiner | |
| 5,072,313 A | * | 12/1991 | Schweitzer et al. | 359/529 |
| 5,287,219 A | * | 2/1994 | Hildebrand et al. | 359/368 |
| 5,321,447 A | * | 6/1994 | Sander et al. | 351/216 |
| 5,333,076 A | * | 7/1994 | Wight | 359/556 |
| 5,438,456 A | * | 8/1995 | Grinblat | 359/835 |
| 5,754,339 A | * | 5/1998 | Kanai et al. | 359/557 |
| 5,986,801 A | * | 11/1999 | Volk et al. | 359/376 |
| 6,598,672 B2 | | 7/2003 | Bell et al. | |
| 6,788,455 B2 | | 9/2004 | Kirchhuebel et al. | |
| 2003/0165012 A1 | | 9/2003 | Straehle et al. | |

FOREIGN PATENT DOCUMENTS

| | | |
|---|---|---|
| DE | 35 39 009 | 5/1987 |
| EP | 0 701 706 B1 | 3/1996 |
| WO | WO 91 15150 | 10/1991 |

* cited by examiner

*Primary Examiner*—Stephone B. Allen
*Assistant Examiner*—Joshua L Pritchett
(74) *Attorney, Agent, or Firm*—Walter Ottesen

(57) ABSTRACT

The invention relates to an image reversion system (500) which enables an image reversion and beam transposition of a plurality of observation beam paths (503*a*, 503*b*, 504*a* and 504*b*) to be carried out simultaneously. The system includes at least one Porro prism system and is designed in such a way that it can be arranged in a convergent beam path. The inventive system is suitable as an image reversion system in an ancillary module for operational microscopes used in ophthalmoscopy due to the low overall height thereof.

22 Claims, 5 Drawing Sheets

IMAGE REVERSION SYSTEM, ANCILLARY OPHTHALMOSCOPY MODULE AND SURGICAL MICROSCOPE

RELATED APPLICATIONS

This application is a continuation application of international patent application PCT/EP 01/10094, filed Sep. 1, 2001, and claiming priority from German patent applications 100 47 617.1, filed Sep. 26, 2000, and 101 40 402.6, filed Aug. 17, 2001.

FIELD OF THE INVENTION

The invention relates to a system for image reversion having a first mirror for deflecting a beam from an incident direction into a first direction which runs tranversely to the incident direction. The image reversion system further includes a second mirror for deflecting the beam, which was deflected at the first mirror, into a second direction which is transverse to the first direction and a third mirror for deflecting the beam, which is deflected at the second mirror, into a third direction which is transverse to the second direction and a fourth mirror for deflecting the beam, which is deflected by the third mirror, into a direction which is transverse to the third direction. The first, second, third and fourth mirrors have respective surface normals which are at an angle to each other and at least two mirrors are formed by a surface of a 90° prism. It is understood that surface normals which are at an angle to each other are surface normals which conjointly define an angle which is different from 0° and 180°. This means that the surface normals are neither parallel nor antiparallel to each other. The invention relates also to an ancillary module of a surgical microscope and a microscope, especially a surgical microscope, which is equipped with such an ancillary module. The ancillary module is equipped with such a system for image reversion.

BACKGROUND OF THE INVENTION

A system for image reversion is disclosed in U.S. Pat. No. 5,009,487. There, a prism system is provided for a binocular surgical microscope for image reversion and lateral exchange of two viewing beam paths. The prism system is built up of eight 90° prisms. In each of the 90° prisms, a prism surface, which lies opposite the 90° angle, operates as a mirror. Each viewing beam path is coupled out by such a 90° prism into a plane perpendicular to the optical axis of the microscope lens system in order to be supplied, image reversed, to the other beam path after a two-time reflection. This system of image reversion is mounted in the microscope between the microscope optical tube and a magnification changer. The system can then be switched into and out of the viewing beam path of the surgical microscope.

The text of Neumann-Schröder entitled "Bauelemente der Optik", Hanser Verlag, Munich (1992), page 174, describes how an image reversion beam path can be made available by multiple reflections at the surfaces of Porro prisms and shortened Porro prisms.

German patent publication 200 21 955 U1 discloses a surgical microscope having an ancillary module which is designed for carrying out surgical procedures in the rear eye section with an ophthalmoscopic magnifier. This ancillary module includes a system for image reversion and is based on a prism construction.

The system is mounted below the surgical microscope main objective and makes an unreversed view of the ocular fundus available to a viewer.

U.S. Pat. No. 5,321,447 discloses a surgical microscope having an ophthalmoscopic ancillary module which is mounted below the microscope main objective as an extension of the microscope tube. This ophthalmoscopic ancillary module has one or several ophthalmoscopic lenses directed toward the objective which function to generate a vertically inverted and laterally inverted image of the ocular fundus of a patient in a first intermediate image plane. The image of this first intermediate image plane is imaged erect and nonreversed into a second intermediate image plane via an optical system for image erection and pupil transposition. The image of this second intermediate image plane can be seen by a microscope viewer through the microscope main objective and a displaceable lens directed toward the microscope main objective. With the ancillary module, the microscope viewer can focus the section of the patient eye which is of interest.

Only a relatively small work space is available to an operator when utilizing such an ophthalmoscopic ancillary module in a surgical microscope. This is so because the ophthalmoscopic lens system has to be mounted closely above the cornea of the eye for imaging the ocular fundus of the eye of the patient. Such ophthalmoscopic ancillary modules are not designed for contact lenses with which the ocular fundus can be made visible in correspondence to an ophthalmoscopic magnifier for which a comparatively large work space is possible for the operator.

The ophthalmoscopic ancillary module, which is described in U.S. Pat. No. 5,321,447, is also not designed for viewing a surgical region by an assistant surgeon with the same quality of viewing as for the primary surgeon. In order to make possible a surgical area companion viewing, the surgical microscope used must be provided with beam coupling units in the region of the microscope tube which split the one viewing beam path into two component beams for the main viewer and the assistant viewer. This configuration, on the one hand, ensures that the main and companion viewers basically see the same image. However, there is a clear brightness loss of the image seen by the main and assistant viewers.

German patent publication 299 05 969 U1 discloses a further stereoscopic surgical microscope wherein ophthalmoscopic magnifiers or contact lenses are used for eye operations for imaging the ocular fundus of a patient eye. This surgical microscope includes an additional lens which can be pivoted into the beam path ahead of the microscope main objective. A system for image reversion which can be pushed in and out is disposed in the microscope optical tube above the magnification changer. This system makes it possible for a surgeon to generate a lateral and pupil correct image of the ocular fundus. This mounting of the system for image reversion has, however, a relatively high microscope assembly as a consequence. This leads to a correspondingly high look-in elevation and a surgeon can only assume an unfavorable work posture. Furthermore, with this construction principle, the microscope image, which is to be seen by a viewer, is not delimited by the size of the microscope main objective but by the dimensioning of the system for image reversion. This has the consequence that a viewer perceives a vignetted or shaded microscope image. Furthermore, if the microscope is, on the one hand, utilized for investigating the ocular fundus of the eye of a patient together with an ophthalmoscopic magnifier or contact glass, and should it then be necessary to remove the ophthalmoscopic magnifier or the contact glass from the beam path for viewing the cornea, then it is necessary to work with changing sharpness adjustments of the microscope. On the one hand, this hinders the surgical sequence and, on the other hand, the focal plane of the optical system is thereby shifted. This last matter has an unwanted magnification change as a consequence for the viewer. Furthermore, with this construction principle it is not possible to correct unwanted imaging errors of additional lenses, ophthalmoscopy magnifiers or contact lenses.

An ancillary module for a stereoscopic surgical microscope is known from German patent publication 3,539,009 wherein the ancillary module includes a system for image reversion and an ophthalmoscopic lens. The system is arranged forward of the microscope main objective. The ocular fundus of the eye is imaged in an intermediate image plane by means of the ophthalmoscopic lens and this intermediate image is located in the ancillary module. The image of this intermediate image plane is projected into the microscope main objective via a field lens and the system for image reversion. Such a microscope configuration causes only a small work space to be provided for an operator and does not make possible a use of contact lenses which are arranged on the eye of the patient. If, during surgery, the ocular fundus of the eye or the vitreous body of the eye of the patient is to be viewed alternately, then the ancillary module has to be removed from the beam path and the focus adjustment of the microscope main objective must be changed.

SUMMARY OF THE INVENTION

It is an object of the invention to provide a system for image reversion with a reduced structural elevation which can be used in an ancillary module for a surgical microscope wherein the ancillary module is designed for carrying out surgery in the rear section of the eye. It is a further object of the invention to provide an ancillary module for a surgical microscope and to provide a microscope which makes possible nonreversed viewing of the cornea and of the ocular fundus with the largest possible work space for a surgeon.

The system for image reversion of the invention is for operating on a beam and includes: a first 90° prism having a base surface defining a first mirror for receiving the beam thereon in an incident direction and deflecting the beam in a first direction transverse to the incident direction; a second 90° prism having a base surface defining a second mirror for deflecting the beam reflected from the first mirror into a second direction transverse to the first direction; a half Porro prism having a first surface defining a third mirror for deflecting the beam reflected from the second mirror into a third direction transverse to the second direction; the half Porro prism having a second surface defining a fourth mirror for deflecting the beam reflected from the third mirror into a fourth direction transverse to the third direction; the first, second, third and fourth mirrors having first, second, third and fourth surface normals, respectively; the surface normals being at an angle to each other; and, the second 90° prism being rotatable about an axis running transversely to the second surface normal so that a tilting of a surface of the second 90° prism can be adjusted to an opposite-lying surface of the first 90° prism.

In such a system according to the invention for image reversion, the surface of the Porro prism, which operates as a mirror, is not simultaneously a surface of a 90° prism. In this way, a compact configuration of the system for image reversion is made possible.

According to an embodiment of the invention, the Porro prism is configured as a shortened Porro prism of the second type. It has been shown that a Porro prism system of the second type is an optical system component which is suitable in an advantageous manner to provide a desired offset between an entering and an exiting beam as is required for a beam transposition. At the same time, an image reversion is effected with the Porro prism system of the second type. A Porro prism system of the second type is configured comparatively compactly. The use of such a prism system in components for surgical microscopes makes it possible to optimize the dimensions of surgical microscopes with respect to the largest possible work space or an unwanted covering of parts of the surgical field. The image reversion and the beam transposition is achieved with optical components which contribute to the total light path of the beams with only a comparatively short optical path length.

The system for image reversion includes at least one mirror which is rotatable about an axis running transversely to the surface normal of the mirror, that is, the mirror is rotatably movable on an axis which is not parallel to the surface normal of the mirror. In this way, an adjustable system for image reversion is provided which is suitable for use in a convergent beam path.

In a further embodiment of the invention, the system for image reversion includes at least one mirror which is displaceable in a direction running transversely to the mirror surface. A direction transverse to the mirror surface is understood to be every direction which is not parallel to the mirror surface. In this way, a system for image reversion is provided with an adjustable beam offset.

In a further embodiment of the invention, the system for image reversion includes at least one mirror which is configured as a boundary surface of a 90° prism. The 90° prism is rotatable about an axis approximately parallel to the boundary surface of the prism. An axis which is approximately parallel to a surface is understood to be every axis which is not perpendicular to this surface. In this way, a simple configuration of the system for image reversion is made possible.

In a further embodiment of the invention, the system for image reversion includes at least two rotatable mirrors and at least two displaceable mirrors. In this way, it is possible to align a beam, which runs through the system for image reversion, with reference to the optical axis of an imaging system.

In another embodiment of the invention, the system for image reversion includes two Porro prism systems which are arranged one within the other to a symmetrical arrangement. In this way, the structural elevation of the system can be minimized.

An ancillary module for surgical microscopes which includes one or two Porro prisms of the second type, can be built up especially compact.

A high image quality for a nonreversed microscope image can therefore be achieved with an ancillary module containing the system for image reversion in accordance with the invention. With an ancillary module having a precisely adjustable system for image reversion arranged in the beam path of a surgical microscope ahead of the microscope main objective, one can compute that limit values for binocular errors in the eye of the viewer are not exceeded.

In eye surgery, a selective use of ophthalmoscopy magnifiers and contact lenses is possible with a focus optical system in the ancillary module which is mounted on the end of the system for image reversion which faces toward the object. Because the focus optical system of the ancillary module is adjustable, the ancillary module itself makes possible a refraction compensation of a patient's eye and can furthermore easily be adapted to different ophthalmoscopy magnifiers or contact lenses and the microscope main objective. Preferably, the focus optical system has at least one converging lens. In this way, it is possible to shift the focus plane of the microscope main objective to which the ancillary module is connected. A corrected focus optical system is provided in that the focus optical system in the ancillary module includes at least one scattering lens. Furthermore, a low structural elevation and small displacement paths of the focus optical system can be achieved in this way. Furthermore, imaging errors can be corrected which are caused by an ophthalmoscopy magnifier or a contact lens. Preferably, the converging lens or the scattering lens is held to be movable along the optical axis of the focus optical system for the ancillary module. With this configuration, the focus plane of the optical system of surgical microscope and ancillary module can be varied without it being necessary to make changes in the adjustments of the surgical microscope. If the system for image reversion and the focus optical system in the ancillary module is designed for being switched into and out of the beam path, then it is possible to switch comfortably back and forth between a viewing of the cornea and a viewing of the ocular fundus of an eye of a patient.

In a further embodiment of the invention, the ancillary module has an ophthalmoscopy magnifier for generating an intermediate image of the ocular fundus of an eye of a patient. In this way, an especially compact ancillary module is provided.

In accordance with another embodiment of the invention, the focal lengths of focus optical system and ophthalmoscopy magnifier are matched to each other in the ancillary module.

It is here understood that, for a switched-in ancillary module, the focal plane of microscope main objective and focus optical system lies in the region of the intermediate image generated by the ophthalmoscopy magnifier. In contrast, for a switched-out system for image reversion, the focus of the surgical microscope comes to rest on the cornea of the eye of the patient without it being necessary to refocus therefor. In this way, an easy adjustment of the ancillary module of the surgical microscope is made possible for eye surgery wherein there must be a back and forth change of viewing between the cornea and the retina.

Because a beam transposition of at least two viewing beam paths is provided in the ancillary module, a stereoscopically correct imaging of the ocular fundus is made possible with a spatial image impression.

An ancillary module which includes a system for beam transposition and image reversion of at least four binocular viewing beam paths permits a companion viewing of a surgical area without this leading to a loss of brightness in the main viewing image.

A surgical microscope, which is equipped with the system for image reversion according to the invention or with the ancillary module, is optimized for carrying out surgery on the rear section of the eye.

BRIEF DESCRIPTION OF THE DRAWINGS

The invention will now be described with reference to the drawings wherein.

DESCRIPTION OF THE PREFERRED EMBODIMENTS OF THE INVENTION

Figure 1:
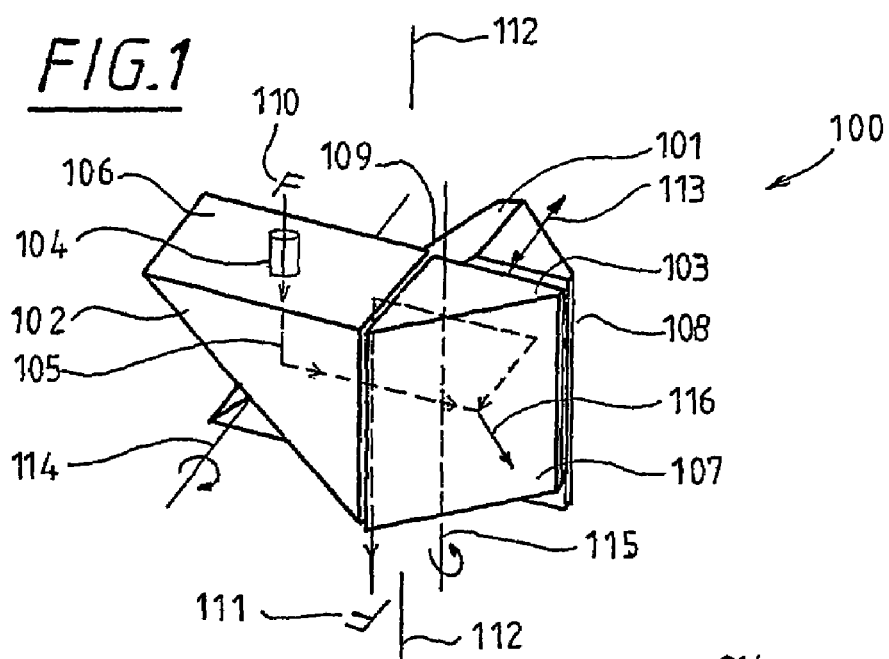
FIG. 1 is a first embodiment of a system for image reversion.

The system for image reversion 100 of FIG. 1 comprises a component prism 101 to which two 90° prisms 102 and 103 are assigned. As the special case of a Porro prism, the component prism 101 is configured as a half, shortened Porro prism of the second type. An incident beam 104 having a beam path 105 passes through the side surface 106 of the component prism 102 and is reflected at the side surface, which lies opposite the 90° angle and acts as a mirror, and is deflected from its incident direction toward the 90° prism 103 with this direction being transverse to the incident direction. In the 90° prism 103, the total reflection at the side surface 107, which acts as a mirror, leads to the deflection of the beam path into the component prism 101. After reflection at the side surfaces 108 and 109 of component prism 101, the companion viewing beam path passes laterally offset through the base surface of the component prism 101. The side surfaces 108 and 109 operate as mirrors.

The surface normals of those sides of the component prism 101 and the two 90° prisms 102 and 103, at which the beam path 105 is deflected, conjointly define angles, namely: the surface normals of those sides of the component prism 101, whereat the beam path 105 is deflected, are at an angle of approximately 120° to each other. The surface normals of the two 90° prisms 102 and 103, whereat a deflection of the beam path 105 occurs, likewise conjointly define an angle of approximately 120°; whereas, the surface normals of the side surfaces 107 and 108 define an angle which lies in the region of 90°.

Because of the reflections at the side surfaces of the system for image reversion 100, a beam path, which images the image 110, effects an inverted image 111. This beam path passes through the system for image reversion 100.

In order to avoid a focus difference and parallax difference between the viewing beam paths when utilizing the system in the viewing beam path of a stereo microscope, the position of the focal planes in the imaging by the various systems, on the one hand, and the orientation of the entry and exit beam path as well as the offset thereof relative to the optical axis 112, on the other hand, are held to be adjustable. The viewing beam paths are guided through various systems for image reversion. With the above, the component prism 101 and the two 90° prisms 102 and 103 are held in a holding frame (not shown) with adjusting devices. These adjusting devices make possible, on the one hand, to displace the component prism 101 back and forth in the direction of an axis 113 transversely to the side surface 108 acting as a mirror in order to be able to adjust the distance of this component prism 101 to the 90° prisms 102 and 103. On the other hand, the 90° prism 102 is held rotatably movable in the holder frame for adjusting about a rotational axis 114 which is parallel to the side surface of the 90° prism 102 which acts as a mirror and lies opposite to the 90° angle. The 90° prism 103 can be moved about a rotational axis 115 which runs transversely to the surface normal of the side surface 107 of the 90° prism 103. The side surface 107 operates as a mirror.

Figure 2:
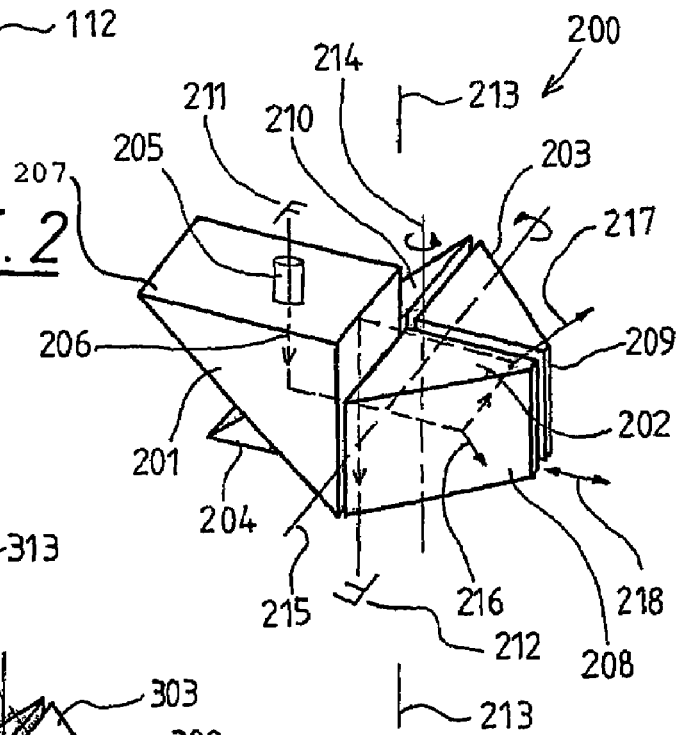
FIG. 2 is a second embodiment of a system for image reversion.

FIG. 2 shows a system for image reversion 200 with four 90° prisms (201, 202, 203, 204). A beam 205 with the beam path 206 passes through the side surface 207 of the 90° prism 201 and is reflected at the side surface lying opposite to the 90° angle and is deflected in a direction toward the 90° prism 202, which direction is transverse to its incident direction. There, the total reflection at the side surface 208 leads to the deflection of the beam path in a transverse direction into the 90° prism 203. After reflection at the side surface 209 of 90° prism 203, the beam path reaches the 90° prism 204 and then leaves the 90° prism 204 laterally offset after a new reflection at side surface 210. In correspondence to the system for image reversion 100 of FIG. 1, the surface normals of those sides of the 90° prisms (201, 202, 203, 204), at which the beam path 206 is reflected, are at an angle to each other.

Due to the reflections at the side surfaces of the system for image reversion 200, a beam path, which images the image 211 passes through the system for image reversion 200, leads to an inverted image 212.

To avoid focus differences and parallax differences between several viewing beam paths, which are guided through various systems for image reversion, when utilizing this system in the viewing beam path of a stereo microscope, on the one hand, the position of the focal planes is held adjustable with the imaging through the various systems for image reversion and, on the other hand, the orientation of entry and exit beam path as well as the offset relative to the optical axis 213 is held adjustable. For the above purpose, a holding frame (not shown) with adjusting devices is provided in which the 90° prisms (201, 202, 203, 204) are accommodated.

The 90° prisms 201 and 204 are mounted immovably in this holding frame; whereas, the 90° prism 202 can be moved for adjustment about a rotational axis 214. This rotational axis 214 is parallel to the side surfaces 208 and 209 of the two 90° prisms 202 and 203. The side surfaces 208 and 209 operate as mirrors. Furthermore, these 90° prisms 202 and 203 can be adjusted in common about a tilt axis 215 in the holding frame. The tilt axis 215 runs transversely to the surface normals 216 and 217 of the side surfaces 208 and 209 of these prisms. These 90° prisms 202 and 203 can additionally be moved in common back and forth along an axis 218 which, in turn, is transverse to the side surfaces 208 and 209 of the prisms 202 and 203.

Figure 3:
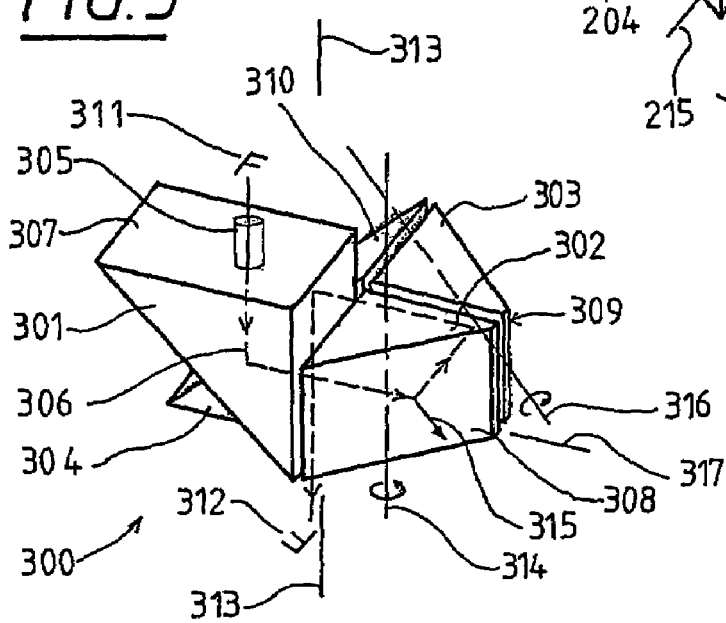
FIG. 3 is a third embodiment of a system for image reversion.

In FIG. 3, a further system for image reversion 300 is shown and corresponds in its configuration substantially to the system for image reversion 200 in FIG. 2. This system, in turn, includes four 90° prisms (301, 302, 303, 304). A beam 305 having beam path 306, which passes through the side surface 307 of 90° prism 301, is reflected at the side surface, which lies opposite the 90° angle, and is deflected into the 90° prism 302. In 90° prism 302, the total reflection at the side surface 308 leads to the deflection of the beam path 306 into the 90° prism 303. The beam path 306 is guided into the 90° prism 304 by reflection at the side surface 309 of 90° prism 303 in order to leave the 90° prism 304 after a new reflection at the side surface 310. Due to the reflections at the side surfaces of the system for image reversion 300, a beam path, which images the image 311, leads to a laterally offset and inverted image 312. The beam path imaging the image 311 passes through the system for image inversion 200.

The position of the focal plane in the imaging via the various systems, on the one hand, as well as the beam offset, which is caused by the system for image reversion 300, and the orientation of the entry beam path and exit beam path relative to an optical axis 313, on the other hand, are, in turn, adjustable. For this purpose, a holding frame (not shown) having adjusting devices is provided wherein the 90° prisms (301, 302, 303, 304) are accommodated. In this holding frame, the 90° prisms 301 and 304 are immovably mounted; whereas, the 90° prism 302 can be moved for adjustment about a rotational axis 314 which is parallel to the side surface 308 of the 90° prism 302 and the 90° prism 303 can be adjusted by carrying out a tilt movement about a rotational axis 316 transverse to the surface normal 315 of the side surface 309. The side surface 308 of the 90° prism 302 acts as a mirror. Furthermore, the 90° prisms 302 and 303 can be moved back and forth in common along an axis 317 in correspondence to the system for image reversion 200 of FIG. 2. The axis 317 is, in turn, transverse to the side surfaces 308 and 309 of the 90° prisms 302 and 303.

Figure 4:
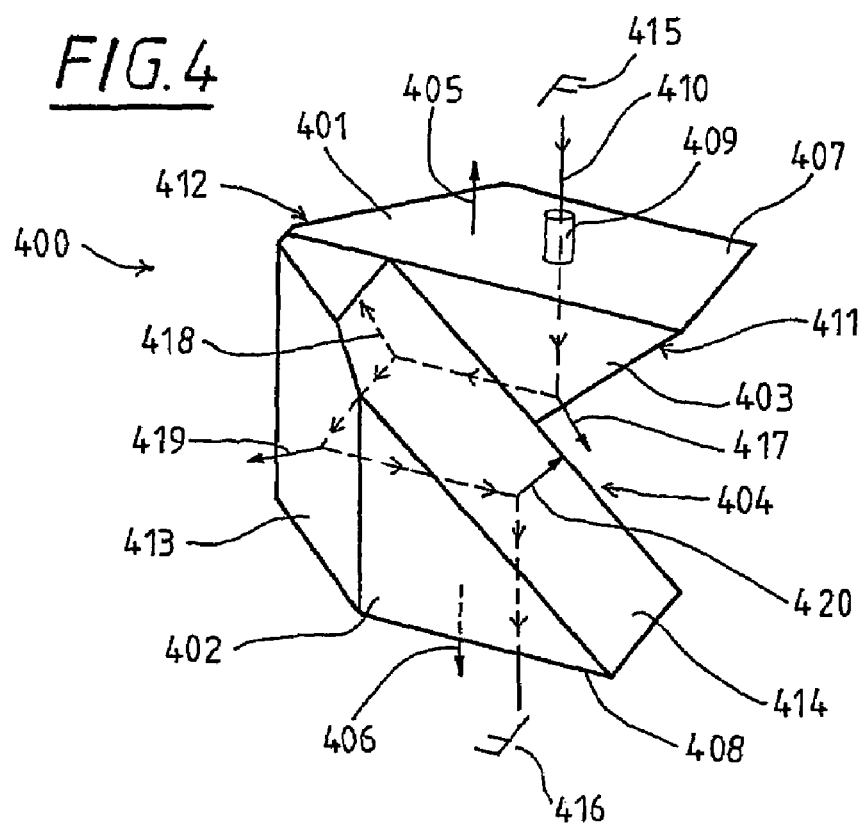
FIG. 4 is a fourth embodiment of a system for image reversion.

FIG. 4 shows a system for image reversion 400 from FIG. 1 which comprises two identical component prisms 401 and 402 which are each configured in the form of half, shortened Porro prisms of the second type in the special case of Porro prisms. The component prisms 401 and 402 lie one against the other at their respective largest side surfaces 403 and 404 so that the surface normals (405, 406) of the mutually corresponding side surfaces (407, 408) are parallel to each other. The surface normals (405, 406) are directed outwardly.

A beam 409 having a beam path 410, which passes through the side surface 407 of component prism 401, is reflected at side surface 411, which acts as a mirror, and is deflected out of its incident direction into a direction, which is transverse to the incident direction, and, in this direction, impinges on the side surface 412 of the component prism 401. In component prism 401, the total reflection at the side surface 412, which acts as a mirror, leads to the deflection of the beam path into the component prism 402 in a direction of the side surface 413 thereof. The beam path is reflected at side surface 413 and is deflected transversely to the side surface 414 of component prism 402. The beam path is, in turn, here reflected in order to leave the system for image reversion 400 via the base surface of the component prism 402. Due to the reflections at the side surfaces of the system for image reversion 400, a beam path passing through the system for image reversion 400 images the image 415 into an inverted image 416 with lateral offset.

In the system for image inversion 400, the surface normals (417, 418) are at an angle of approximately 120° to each other. The same applies to the surface normals 419 and 420; whereas, the surface normals 418 and 419 are orientated to each other at an angle lying in the region of 90°. The surface normals of those sides of the component prisms 401 and 402 at which the beam path 410 is deflected, are, in turn, at an angle to each other.

Figure 5A:
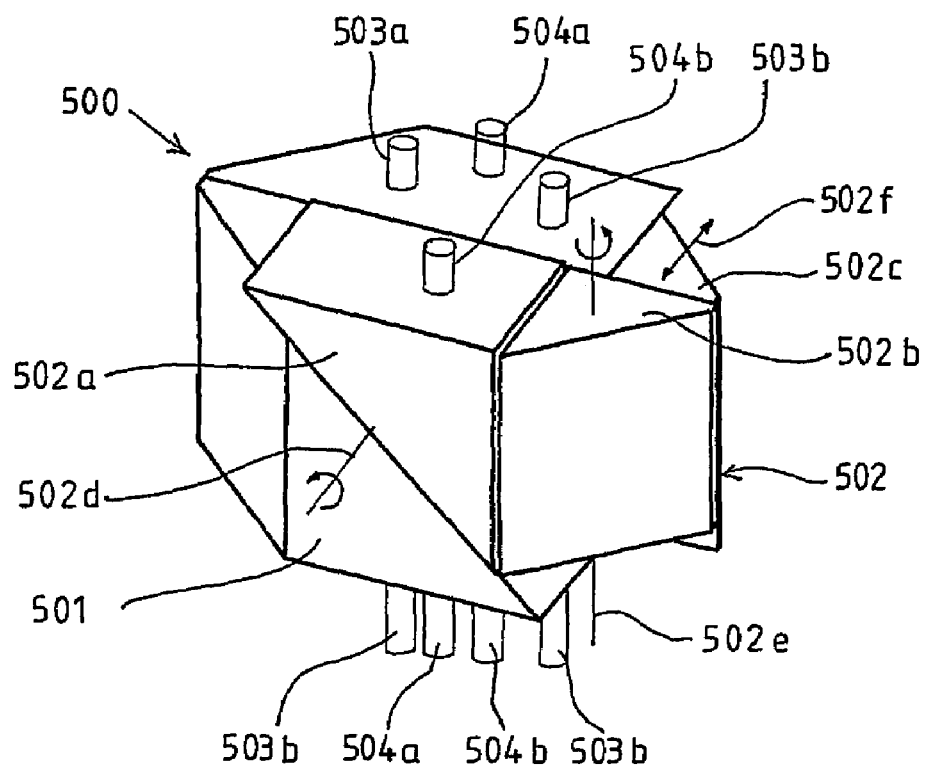
FIG. 5a is a schematic of a first embodiment of a system for beam transposition and image reversion for a binocular main viewing beam path and a companion viewing beam path.

FIG. 5a shows a system for simultaneous beam transposition and image reversal for a binocular main viewing beam path and a binocular companion beam path. The system for beam transposition and image inversion 500 is built up from a first system for image inversion 501 which corresponds to that system for image inversion 400 from FIG. 4 and includes a system for image inversion 502 with a holding frame (not shown) which is built up in correspondence to the system for image inversion 100 of FIG. 1. This first system for image inversion 501 and the second system for image inversion 502 are assembled to a symmetric arrangement which is mounted on a holder (not shown in FIG. 5a). The holding frame of the system for image inversion 502 is fixed on this holder. The holding frame holds the 90° prisms 502a and 502b as well as the component prism 502c which is configured as a shortened Porro prism. The 90° prism 502a can be moved for adjustment about the rotational axis 502d and the 90° prism 502b can be moved about rotational axis 502e for adjustment. Furthermore, it is possible to displace the component prism 502c along the axis 502f in the holding frame.

For a binocular beam path having beams 503a and 503b, the system for image inversion 501 operates as a system for image inversion as well as also for image transposition. For the beam 504a of a binocular beam path, which comprises the beams 504a and 504b, the system for image inversion 501 provides, in contrast, only an image reversal with simultaneous lateral offset. A system for beam transposition and image inversion 500 of four beam paths is provided in that the beam 504b of the corresponding binocular beam path is guided over the system for image inversion 502.

Due to the adjusting possibility of the 90° prisms 502a and 502b as well as the component prism 502c in the system for image inversion 502, the focus and parallax differences for the beam path from the beams 504a and 504b can be compensated by corresponding adjustment of the prisms. In this way, the system for beam transposition and image inversion 500 can be adjusted precisely especially for an arrangement in a convergent beam path as is the case, for example, forward of the main objective of a surgical microscope.

Figure 5B:
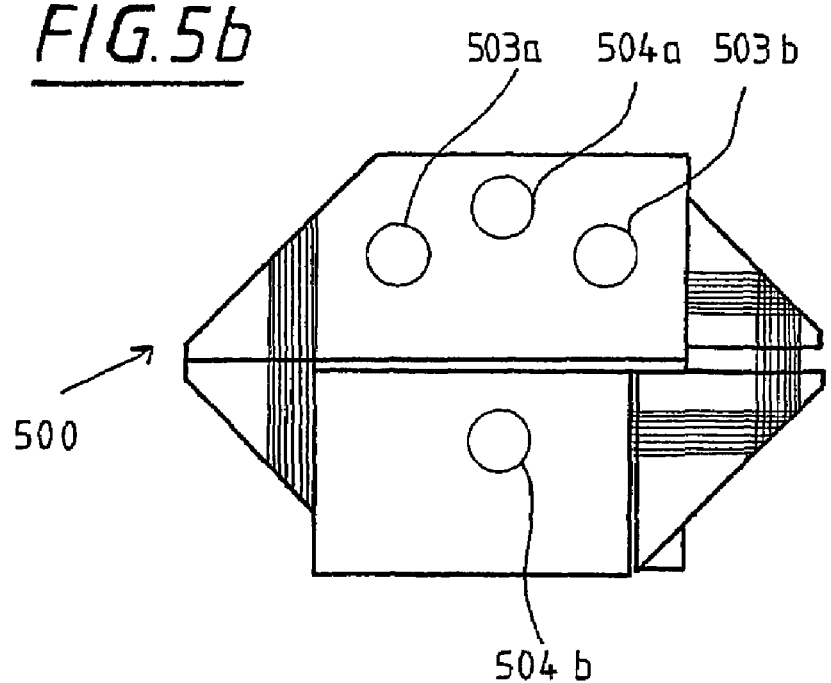
FIG. 5b is a front view of the first embodiment of the system for beam transposition and image reversion.

FIG. 5b shows the system for beam transposition and image inversion 500 in a front elevation view. The viewing beams 503a and 503b as well as 504a and 504b can be held to a very tight space which, for example, is determined by the diameter of a surgical microscope main objective.

Figure 6:
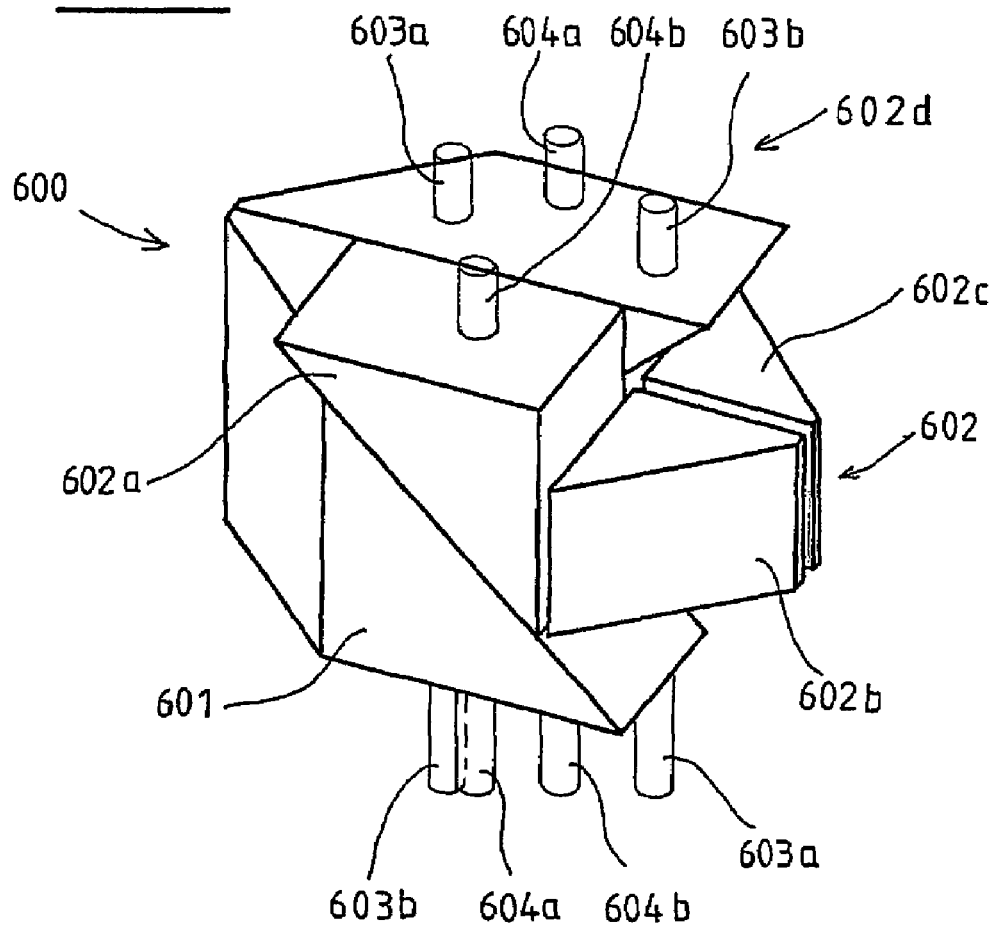
FIG. 6 is a schematic of a second embodiment of a system for beam transposition and image reversion for a binocular main viewing beam path and a companion viewing beam path.

In FIG. 6, a further embodiment 600 for a system for simultaneous beam transposition and image inversion of a binocular main viewing beam path and a binocular companion viewing beam path is shown. The system for beam transposition and image inversion 600 is, in turn, built up from a first system for image inversion 601 which corresponds to that system for image inversion 400 of FIG. 4 and includes a system for image inversion 602 having a holding frame (not shown) which is built up in correspondence to the system for image inversion 200 of FIG. 2 or the system for image inversion 300 of FIG. 3. This first system for image inversion 601 and the second system for image inversion 602 are joined to a symmetric arrangement. The system for image transposition and image inversion 600 is, in turn, assembled on a holder not shown in FIG. 6. The holding frame of the system for image inversion 602 is mounted on this holder. This holding frame accommodates the four 90° prisms (602a, 602b, 602c, 602d). The position of the 90° prisms can be adjusted in correspondence to the alternate configurations for movement axes explained with respect to FIGS. 2 and 3.

The system for image inversion 601 operates for a binocular beam path with beams 603a and 603b as a system for beam transposition and image inversion. For the beam 604a of a binocular beam path, the system functions, in contrast, only as a system for image inversion which simultaneously causes a lateral offset of the beam path. The binocular beam path comprises the beams 604a and 604b. A system for the simultaneous beam transposition and image inversion 600 of four beam paths is provided in that the beam 604b of the corresponding binocular beam path is guided via the system for image inversion 602.

Because of the adjusting possibility of the four 90° prisms (602a, 602b, 602c, 602d) in the system for image inversion 602, it is, in turn, possible to compensate focus and parallax differences for the beam path of beams 604a and 604b via a corresponding adjustment of the prisms so that the system for beam transposition and image inversion 600 likewise can be precisely adjusted which makes possible especially an arrangement in a convergent beam path.

Figure 7:
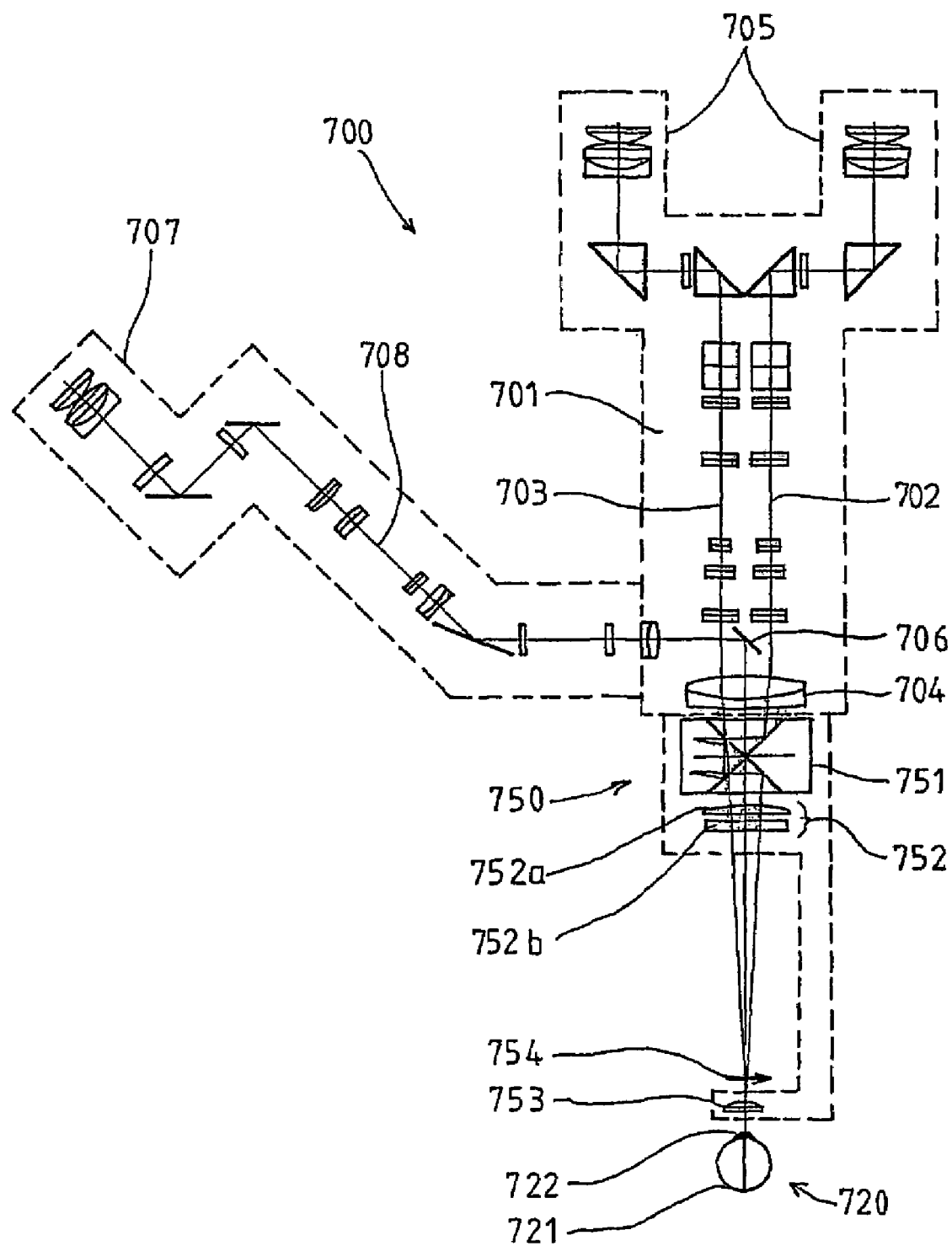
FIG. 7 is a schematic of a surgical microscope having an ancillary module.

FIG. 7 shows a microscope 700 configured as a stereoscopic surgical microscope having binocular viewing beam paths (702, 703, 708) for a main viewer and a companion viewer. The microscope 700 includes a tube 701 having respective lens systems for the left and right viewing beam paths (702, 703). The left viewing beam path 702 and the right viewing beam path 703 pass through a common microscope main objective 704. For a main viewer, which is not shown in FIG. 1, an ocular unit 705 is provided in the microscope 700. With this ocular unit 705, a surgical region on a human eye 720 can be viewed.

A deflecting mirror system 706 is provided in the tube 701 of the surgical microscope 700 above the microscope main objective 704. This is to enable a companion viewer to likewise view the surgical area via an ocular unit 707 and a binocular viewing beam path 708. The binocular viewing beam path 708, in turn, includes left and right viewing beam paths which pass through the microscope main objective 704 offset to the left and right viewing paths 702 and 703. In this way, a companion viewing of the surgical area is made possible without a loss in brightness compared to the use of beam splitter techniques.

An ancillary module 750 for nonreversed and image correct imaging of the ocular fundus 721 of the eye 720 is provided on the tube 701 of the surgical microscope 700 below the microscope main objective 704. This ancillary module 750 is connected to the tube 701 with a bayonet connection for rapid and easy exchange. The ancillary module 750 includes a system for image inversion and beam transposition 751, a focusing optic 752 as well as an ophthalmoscopic magnifier 753. The system for image inversion and beam transposition 751 in the ancillary module 750 is designed for simultaneous image inversion and beam transposition of four binocular viewing beam paths. As shown in FIG. 7, the beam path between the main objective 704 and the ophthalmoscopic magnifier 753 is a convergent beam path. The system 751 is mounted in this convergent beam path and is arranged in the region of the ancillary module 750 facing toward the microscope main objective. The focus optic 752 is disposed below the system for image inversion and beam transposition 751 in the region of the ancillary module 750 which faces toward the area of surgery. The focus optic 752 includes a converging lens 752a and a scatter lens 752b. An ophthalmoscopic magnifier 753 is assigned to the focus optic 752.

The microscope main objective 704 of the microscope 700 is adjusted sharply to the retina 722 for carrying out a surgical procedure on a human eye 720.

The focus optic 752 focuses the viewing beam paths (702, 703, 708) into an intermediate plane 754 into which the ophthalmoscopic magnifier 753 casts a reversed image of the ocular fundus 721. The position of the intermediate image plane 754 is determined, on the one hand, by the refractive power of the ophthalmoscopic magnifier 753 itself and is determined, on the other hand, by the distance of the ophthalmoscopic magnifier 753 from the eye, the eye geometry itself and the refractive power of the eye lenses. The focus optic 752 is configured to be adjustable in that the converging lens 752a is displaceably mounted along the optical axis of the focus optic 722. Accordingly, the work distance of the microscope 700 with the ancillary module 750 from a human eye 720 can be maintained so as to be adjustable and it is possible to undertake adaptations to an ametropic or aphakic eye of the patient.

It is also possible to configure the focus optic such that the scattering lens is displaceable and the converging lens is held to be immovable or both lenses can be displaced along the optical axis of the focus optic.

Figure 8:
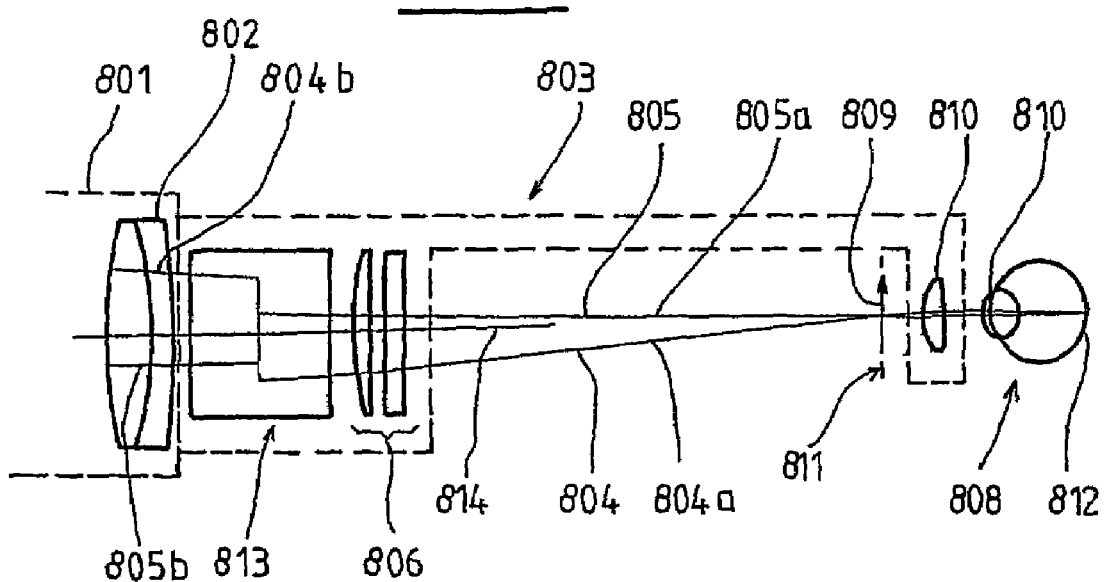
FIG. 8 is a schematic section view of the beam path through the surgical microscope main objective with ancillary module wherein a system for beam transposition and image reversion is switched into the beam path; and, FIG. 9 is a schematic section view of the beam path through a surgical microscope main objective with ancillary module wherein a system for beam transposition and image reversion is switched out of the beam path.

FIG. 8 shows a section of the lower region 801 of the tube of the microscope 700 from FIG. 7 with a course of the viewing beam paths (804, 805) for a companion viewer.

The binocular viewing beam paths (804, 805) passing through the main objective 802 for the viewing pupils of the companion viewer are adjusted with the focus optic 806 to the intermediate image 809 of the ophthalmoscopic magnifier 810 with the microscope main objective 802 being focused on the retina 812 of the patient eye 808. The ophthalmoscopic magnifier 810 casts a reversed image of the ocular fundus 812 into the intermediate image plane 811.

The system for image reversion and beam transposition 813 effects an image reversal of the reversed image of the ocular fundus 812 in the intermediate image plane 811 for each of the binocular viewing beam paths. Viewed from the intermediate image plane 811, the beam path 805a (running above the optical axis 814 of the focus optic 806) is deflected in the system for image reversion and beam transposition 813 reversed into a beam path 805b which runs below the optical axis 814 of the focus optic 806. A beam path 804a, which runs below the optical axis 814 of the focus optic 806, is converted by the system for image reversion and beam transposition 813 into a beam path 804b which runs above the optical axis 814 of the focus optic 806. Correspondingly, and viewed from the intermediate image plane 811, the system for image reversion and beam transposition 813 deflects a beam path (not shown in FIG. 2), which runs to the left of the optical axis 814 of the focus optic, into a beam path lying to the right of this axis. A beam path to the right of the optical axis 814 of the focus optic is deflected by the system for image reversion and beam transposition 813 into a beam path running to the left of this axis. Due to the stereoscopic course of the viewing beam paths, there results an unreversed and pupil correct image of the ocular fundus 812 with spatial impression for both the main viewer and the companion viewer.

In the ancillary module 803, the ophthalmoscopic magnifier 810, focus optic 806 and the system for image reversion and beam transposition 813 can be switched into and out of the beam path, for example by sliding or pivoting, by means of a mechanism (not shown).

Figure 9:
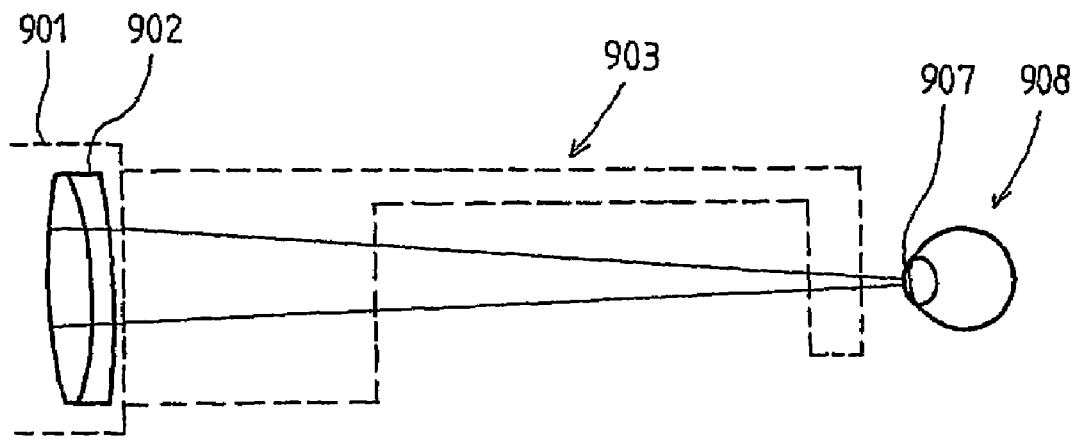

FIG. 9 shows a section of the lower region of the tube 901 of microscope 700 of FIG. 7 with the ancillary module 903 connected to the microscope main objective 902. Here, the system for image reversion, the focus optic and the ophthalmoscopic magnifier are switched out of the beam path. In this case, the focus plane of the viewing beam paths corresponds to that of the microscope main objective and lies at the cornea 907 of the eye 908 of the patient being examined.

As in the system for image reversion and beam transposition, the ancillary module 903 includes respective pivot or displacement mechanisms for switching the ophthalmoscopic magnifier and the focus optic 906 into and out of the beam path. As an alternative to this embodiment, it is possible to provide a mechanism for removing the ancillary module in total from the beam path. Such mechanisms advantageously have controllable drives.

With the system for beam transposition and image reversion, which is designed for four viewing beam paths, a binocular companion viewing of the area of surgery of equal quality at a 0° viewing angle and at the same stereo angle as the main viewer can be provided without brightness loss.

In that the viewing beam paths pass through the microscope main objective independently of each other, the companion viewing of the field of surgery is possible without brightness loss for the main and companion viewer compared to the use of beam splitter techniques.

Instead of designing the system for image reversion and beam transposition for an image reversal and a beam transposition of four binocular viewing beam paths, it is also possible to configure the system only for image inversion and beam transposition of three viewing beam paths. For example, image reversion and beam transposition for two binocular main viewing beam paths and one companion beam path can be provided. It is also possible to provide only an image inversion for one or two viewing beam paths. In this case, however, no spatial microscope image would be offered to the viewer. Optionally, such a system for image reversion can also be designed for one main viewing beam path and three companion beam paths.

A modified embodiment (not shown) of the ancillary module can be designed for adding to a microscope main objective and is designed for imaging the ocular fundus of the eye of a patient for the use with an external ophthalmoscopic magnifier or a contact lens. Such an ancillary module is therefore configured without an ophthalmoscopic magnifier. However, the focus optic in the ancillary module makes possible a focusing onto the intermediate image of the eye of the patient generated with the ophthalmoscopic magnifier or contact lens.

The international patent application PCT/EP 01/10094, filed Sep. 1, 2001, on which this present application is based, is incorporated herein by reference.

It is understood that the foregoing description is that of the preferred embodiments of the invention and that various changes and modifications may be made thereto without departing from the spirit and scope of the invention as defined in the appended claims.

What is claimed is:

1. An ancillary module for mounting to a microscope main objective defining a focal length, the ancillary module having an end facing toward said main objective and comprising:

an adjustable focus optic system for varying said focal length of said main objective along a convergent beam path;

a system for image reversion assigned to said focus optic system and being mounted in said convergent beam path;

said system for image reversion being disposed on said end of said ancillary module facing toward said main objective to facilitate mounting said ancillary module to said main objective;

said system for image reversion being configured as a system for beam transposition of at least two binocular viewing beam paths;
said ancillary module being arranged below said main objective in said convergent beam path;
wherein said system compensates focus and parallax differences of said at least two binocular viewing beam paths; and,
wherein said system for image reversion can be switched into and out of the beam paths.

2. The ancillary module of claim 1, wherein said system for beam transposition includes:
(i) a first 90° prism having a base surface defining a first mirror for receiving the beam thereon in an incident direction and deflecting said beam in a first direction transverse to said incident direction;
(ii) a second 90° prism having a base surface defining a second mirror for deflecting said beam reflected from said first mirror into a second direction transverse to said first direction; and,
(iii) a half Porro prism having a first surface defining a third mirror for deflecting said beam reflected from said second mirror into a third direction transverse to said second direction;
said half Porro prism having a second surface defining a fourth mirror for deflecting said beam reflected from said third mirror into a fourth direction transverse to said third direction;
said first, second, third and fourth mirrors having first, second, third and fourth surface normals, respectively;
said surface normals being at an angle to each other; and,
said second 90° prism being rotatable about an axis running transversely to said second surface normal so that a tilting of a surface of said second 90° prism can be adjusted to an opposite-lying surface of said first 90° prism so as to adjust an optical path length through said system.

3. The ancillary module of claim 2, wherein at least one of said mirrors is displaceable in a direction transverse to the surface of said one mirror.

4. The ancillary module of claim 2, wherein said second 90° prism is rotatable about an axis approximately parallel to a surface thereof.

5. The ancillary module of claim 2, wherein at least two of said mirrors are rotatably mounted and at least two of said mirrors are displaceably mounted.

6. The ancillary module of claim 2, wherein said half Porro prism is a Porro prism assembly which comprises two Porro prism systems coupled to each other to form a symmetrical arrangement.

7. The ancillary module of claim 1, wherein said system for beam transposition includes:
(i) a first 90° prism having a base surface defining a first mirror for receiving said beam thereon in an incident direction and deflecting said beam in a first direction transverse to said incident direction;
(ii) a second 90° prism having a base surface defining a second mirror for deflecting said beam reflected from said first mirror into a second direction transverse to said first direction;
(iii) a third 90° prism having a surface defining a third mirror for deflecting said beam reflected from said second mirror into a third direction transverse to said second direction; and,
(iv) a fourth 90° prism having a surface defining a fourth mirror for deflecting said beam reflected from said third mirror into a fourth direction transverse to said third direction;
said third and fourth 90° prisms conjointly defining a half Porro prism;
said first, second, third and fourth mirrors having first, second, third and fourth surface normals, respectively;
said surface normals being at an angle to each other; and,
said second 90° prism being rotatable about an axis running transversely to said second surface normal so that a tilting of a surface of said second 90° prism can be adjusted to an opposite-lying surface of said first 90° prism so as to adjust an optical path length through said system.

8. The ancillary module of claim 7, wherein at least one of said mirrors is displaceable in a direction transverse to the surface of said one mirror.

9. The ancillary module of claim 7, wherein said second 90° prism is rotatable about an axis approximately parallel to a surface thereof.

10. The ancillary module of claim 7, wherein at least two of said mirrors are rotatably mounted and at least two of said mirrors are displaceably mounted.

11. The ancillary module of claim 7, wherein said half Porro prism is a Porro prism assembly which comprises two Porro prism systems coupled to each other to form a symmetrical arrangement.

12. The ancillary module of claim 1, wherein said system for beam transposition includes:
(i) a first 90° prism having a base surface defining a first mirror for receiving said beam thereon in an incident direction and deflecting said beam in a first direction transverse to said incident direction;
(ii) a second 90° prism having a base surface defining a second mirror for deflecting said beam reflected from said first mirror into a second direction transverse to said first direction; and,
(iii) a half Porro prism having a first surface defining a third mirror for deflecting said beam reflected from said second mirror into a third direction transverse to said second direction;
said half Porro prism having a second surface defining a fourth mirror for deflecting said beam reflected from said third mirror into a fourth direction transverse to said third direction;
said first, second, third and fourth mirrors having first, second, third and fourth surface normals, respectively;
said surface normals being at an angle to each other;
said half Porro prism being displaceable back and forth in the direction of an axis transversely to said first surface of said half Porro prism;
said second 90° prism being rotatable about a first axis running transversely to said second surface normal so that a tilting of a surface of said second 90° prism can be adjusted to an opposite-lying surface of said first 90° prism so as to adjust an optical path length through said system; and,
said second 90° prism being rotatable about a second axis running transversely to said second surface normal.

13. The ancillary module of claim 12, wherein at least one of said mirrors is displaceable in a direction transverse to the surface of said one mirror.

14. The ancillary module of claim 12, wherein said second 90° prism is rotatable about an axis approximately parallel to a surface thereof.

15. The ancillary module of claim 12, wherein at least two of said mirrors are rotatably mounted and at least two of said mirrors are displaceably mounted.

16. The ancillary module of claim 12, wherein said half Porro prism is a Porro prism assembly which comprises two Porro prism systems coupled to each other to form a symmetrical arrangement.

17. The ancillary module of claim 1, wherein said system for beam transposition includes:
   (i) a first 90° prism having a base surface defining a first mirror for receiving said beam thereon in an incident direction and deflecting said beam in a first direction transverse to said incident direction;
   (ii) a second 90° prism having a base surface defining a second mirror for deflecting said beam reflected from said first mirror into a second direction transverse to said first direction;
   (iii) a third 90° prism having a surface defining a third mirror for deflecting said beam reflected from said second mirror into a third direction transverse to said second direction; and,
   (iv) a fourth 90° prism having a surface defining a fourth mirror for deflecting said beam reflected from said third mirror into a fourth direction transverse to said third direction;
   said third and fourth 90° prisms conjointly defining a half Porro prism;
   said first, second, third and fourth mirrors having first, second, third and fourth surface normals, respectively;
   said surface normals being at an angle to each other;
   said second 90° prism being rotatable about a first axis running transversely to said second surface normal so that a tilting of a surface of said second 90° prism can be adjusted to an opposite-lying surface of said first 90° prism so as to adjust an optical path length through said system;
   said third 90° prism being rotatable about a second axis running transversely to said third surface normal; and,
   said second 90° prism and said third 90° prism being movable back and forth along an axis which is transverse to said surface defining said second mirror and said surface defining said third mirror.

18. The ancillary module of claim 17, wherein at least one of said mirrors is displaceable in a direction transverse to the surface of said one mirror.

19. The ancillary module of claim 17, wherein said second 90° prism is rotatable about an axis approximately parallel to a surface thereof.

20. The ancillary module of claim 17, wherein at least two of said mirrors are rotatably mounted and at least two of said mirrors are displaceably mounted.

21. The ancillary module of claim 17, wherein said half Porro prism is a Porro prism assembly which comprises two Porro prism systems coupled to each other to form a symmetrical arrangement.

22. The ancillary module of claim 1, wherein said system for image reversion is configured as a system for beam transposition of at least four binocular viewing beam paths.

* * * * *